(12) United States Patent
Tan et al.

(10) Patent No.: US 8,168,447 B2
(45) Date of Patent: May 1, 2012

(54) MULTIPLE COMPONENT NANOPARTICLES FOR MULTIPLEXED SIGNALING AND OPTICAL ENCODING

(75) Inventors: Weihong Tan, Gainesville, FL (US); Lin Wang, Westfield, IN (US); Chaoyong Yang, El Cerrito, CA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 12/066,308

(22) PCT Filed: Oct. 10, 2006

(86) PCT No.: PCT/US2006/039535
§ 371 (c)(1),
(2), (4) Date: Sep. 28, 2008

(87) PCT Pub. No.: WO2007/044711
PCT Pub. Date: Apr. 19, 2007

(65) Prior Publication Data
US 2009/0017476 A1    Jan. 15, 2009

Related U.S. Application Data

(60) Provisional application No. 60/724,689, filed on Oct. 7, 2005.

(51) Int. Cl.
*G01N 33/552* (2006.01)
(52) U.S. Cl. ............ 436/527; 435/6.1; 435/7.5; 436/524
(58) Field of Classification Search .................. None
See application file for complete search history.

(56) References Cited

U.S. PATENT DOCUMENTS

| | | | |
|---|---|---|---|
| 5,674,690 A * | 10/1997 | Kolodny et al. ............... 435/7.1 |
| 5,852,191 A * | 12/1998 | Karandikar et al. ............ 546/13 |
| 5,874,214 A | 2/1999 | Nova et al. | |
| 6,023,540 A * | 2/2000 | Walt et al. ...................... 385/12 |
| 6,514,295 B1 * | 2/2003 | Chandler et al. ................. 8/607 |
| 6,548,264 B1 * | 4/2003 | Tan et al. ..................... 435/7.21 |
| 6,696,304 B1 * | 2/2004 | Davies ......................... 436/518 |
| 6,924,116 B2 | 8/2005 | Tan et al. | |
| 2004/0067503 A1 | 4/2004 | Tan et al. | |
| 2005/0052646 A1 | 3/2005 | Wohlstadter et al. | |

FOREIGN PATENT DOCUMENTS

| | | |
|---|---|---|
| WO | WO 99/67641 | 12/1999 |
| WO | WO 00/39587 | 7/2000 |
| WO | WO 2005/001872 | 1/2005 |

OTHER PUBLICATIONS

Anaspec <http://web.archive.org/web/20040725071315/http://www.anaspec.com/products/productcategory.asp?id=314>, published Jul. 25, 2004, accessed Jan. 16, 2009.*
Dance et al. Supramolecular motifs: sextuple aryl embraces in crystalline [M(2,2'-bipy)3] and related complexes. J. Chem. Soc., Dalton Trans., 1998, pp. 1341-1350.*
Santra et al. Conjugation of biomolecules with luminophore-doped silica nanoparticles for photostable biomarkers. Anal. Chem., 2001, vol. 73, pp. 4988-4993.*
Wang, L. et al., "Dual-Luminophore-Doped Silica Nanoparticles for Multiplexed Signaling," Nano Letters, 2005, vol. 5, No. 1, pp. 37-43.

* cited by examiner

*Primary Examiner* — Chris L Chin
(74) *Attorney, Agent, or Firm* — Saliwanchik, Lloyd & Eisenschenk

(57) ABSTRACT

The present invention provides multiple-luminophore silica nanoparticles for multiplexed signaling in bioanalysis. In specific embodiments, two inorganic luminophores, Tris(2,2'-bipyridyl)osmium(II) bis(hexafluorophosphate) (OsBpy) and Tris(2,2'-bipyridyl)dichlororuthenium(II) hexahydrate (RuBpy), or three organic luminophores 5-Fluorescein isothiocyanate (5-FITC), 5-carboxyrhodamine 6G, succinimidyl ester (5-CR6G, SE), 6-carboxy-X-rhodamine, succinimidyl ester (6-ROX, SE) can be simultaneously entrapped inside silica nanoparticles at controlled ratios, with desirable sizes and required surface functionality. Single-wavelength excitation with multiple emission endows the nanoparticles with optical encoding capability for rapid and high-throughput multiplexed detection.

9 Claims, 7 Drawing Sheets

MULTIPLE COMPONENT NANOPARTICLES FOR MULTIPLEXED SIGNALING AND OPTICAL ENCODING

CROSS-REFERENCE TO A RELATED APPLICATION

This application is a National Stage Application of International Application Number PCT/US2006/039535, filed Oct. 10, 2006; which claims the benefit of U.S. Provisional Application Ser. No. 60/724,689, filed Oct. 7, 2005, in their entirety.

GOVERNMENT SUPPORT

The subject invention was made with government support under NIH Grant No. GM-66137, NIH Grant No. NS-045174 and NSF Grant No. EF-0304569. The government has certain rights in the invention.

BACKGROUND OF THE INVENTION

The rapid and accurate detection of trace amounts of organisms such as pathogenic bacteria is important in food and water safety, clinical diagnosis, and military/civilian warfare. Recently, there has been much interest in the identification of various microorganisms due to the increased risks of terrorism via biological warfare agents.

*Escherichia coli* O157:H7 (*E. coli* O157:H7) is one of the most dangerous food borne bacterial pathogens. It is commonly found in raw beef, fruits, vegetables, salad bar items, salami, and other food products. Outbreaks of *E. coli* O157:H7 infections have caused serious illnesses and led to a significant number of deaths. Therefore, in order to prevent accidental outbreaks or intentional terrorist acts, early detection of trace amounts of *E. coli* O157:H7 as well as other pathogenic microorganisms is critical.

The key requirements for a detection technique to be used for the early detection of microorganisms are specificity, speed, and sensitivity. Conventional detection methods provide qualitative and quantitative information in the presence of substantial amounts of organisms such as bacterial species. However, time constraints and ease of on-site analysis are major limitations because many of these methods rely on the ability of microorganisms to grow into visible colonies over time in special growth media, which may take about 1-5 days. Moreover, detection of trace amounts of bacteria typically requires amplification or enrichment of the target bacteria in the sample. These methods tend to be laborious and time-consuming because of the complicated assay procedures.

Recently, attempts have been made to improve conventional bacterial detection methods to reduce the assay time. One of these efforts has been in the modification and automation of conventional methods. In addition, many developments have evolved to improve detection techniques; for example: direct epiluminescent filter technique (DEFT), mass spectrometry-based methods, and counting and identification test kits. One of the most promising techniques is flow cytometry, which is able to detect $10^2$-$10^3$ *E. coli* O157:H7 cells/mL within 1 hour based on luminescence signal in a flow system. Though the detection time is dramatically reduced, sensitivity improvement is still a challenge.

Development of multiplexed bioassays has recently become an area of rapidly expanding interest and application. Compared to single target detection methods, multiplexed assays reduce the time and cost per analysis, allow for simpler assay protocols, decrease the sample volumes required, and make comparison of samples feasible and measurements reproducible and reliable. Many disease diagnoses and biomedical studies require information from multiple targets such as numerous proteins and genes. Multiplexed assays are thus crucial to complement advances in genomics and proteomics to allow a large number of nucleic acids and proteins to be rapidly screened. Oligonucleotide microarrays and protein arrays can handle a high degree of multiplexed detection using spatially resolved measurements, but the experimental equipment and detection systems are generally not convenient to use on a routine basis, cannot be used to monitor real-time or near-real-time events and cannot be used for biological sample imaging.

Multiplexed microsphere-based flow cytometry assays offer several advantages such as flexibility in target selection, fast binding kinetics and well-controlled binding conditions. Both fluorophores and quantum dots have been embedded into polymer microbeads for high-capacity spectral coding. With the unique advantage of size-tunable emission and broad excitation properties, quantum dots have the potential to be a suitable luminophore for wavelength and intensity multiplexing. However, it is not easy to carry out parallel coding on the nanometer scale.

Because many biological systems, including viruses, membranes, and protein complexes, are natural nanostructures, a need remains for the development of nanometer scale signaling markers with multiplex capability.

BRIEF SUMMARY OF THE INVENTION

The present invention provides dual-luminophore and triple-luminophore silica nanoparticles (NPs) for multiplexed signaling in bioanalysis.

As used herein, the word "nanoparticle" or "NP" means a particle having a diameter of between about 1 and 1000 nm. Similarly, by the term "nanoparticles" or "NPs" is meant a plurality of particles having an average diameter of between about 1 and 1000 nm.

In a specific embodiment, two inorganic luminophores, Tris(2,2'-bipyridyl)osmium(II) bis(hexafluorophosphate) (OsBpy) and Tris(2,2'-bipyridyl)dichlororuthenium(II) hexahydrate (RuBpy), or three organic luminophores [5-Fluorescein isothiocyanate] (5-FITC), [5-carboxyrhodamine 6G, succinimidyl ester] (5-CR6G, SE) and [6-carboxy-X-rhodamine, succinimidyl ester] (6-ROX, SE) are simultaneously entrapped inside silica NPs at precisely controlled ratios, with desirable sizes and required surface functionality. Single-wavelength excitation with multiple emission endows the NPs with optical encoding capability for rapid and high-throughput multiplexed detection.

The NPs can be prepared with sizes ranging from a few nanometers or less to a few hundred nanometers or more, with specific ratios of luminescence intensities at two well resolved wavelengths and with reproducibility.

By reference to the "size" of a nanoparticle is meant the length of the largest straight dimension of the nanoparticle. For example, the size of a perfectly spherical nanoparticle is its diameter.

The NPs of the subject invention also possess unique properties of high signal amplification, excellent photostability and easy surface bioconjugation for highly sensitive measurements when used as signaling markers.

A further aspect of the subject invention provides a simplified ligand binding system using avidin-biotin.

DETAILED DISCLOSURE OF THE INVENTION

Figure 1:
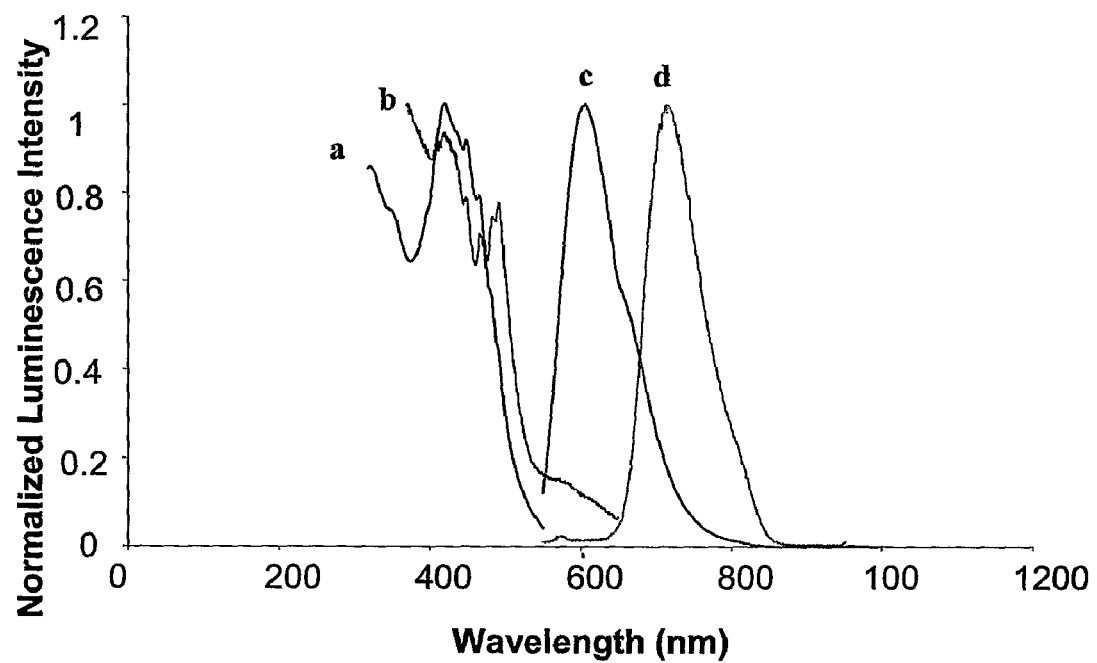
FIG. 1 shows the excitation and emission spectra of RuBpy and OsBpy dyes on a spectrofluorometer.

One embodiment of the present invention provides bioconjugated nanoparticles (NPs) for parallel and high-throughput signaling of biomolecules formed by employing a dual-dye based microemulsion process or a triple-dye based Stöber process.

One embodiment of a method of the invention includes simultaneously doping a plurality of kinds of dye molecules into NPs at precisely controlled ratios. The resulting NPs exhibit well-resolved multiple emissions with single-wavelength excitation. Thus, a multiplex analysis of the present invention is able to use a single wavelength excitation to provide multiple wavelength emissions. Such an arrangement provides for ease of operation.

Exemplified systems of the present invention use the luminescence intensity ratio of two inorganic or three organic types of dye molecules embedded inside a NP. Intensity ratio analysis is effectively used in bioanalysis and bioimaging to provide reproducible measurements and minimize potential problems such as photobleaching. Coupling with flow cytometry or optical microscope, the NPs of the present invention enable very rapid, highly selective and highly sensitive multiplexed bioassays and optical encoding. The system can be used to target biological matter such as bacteria, DNA, mRNA, proteins, antigens and antibodies, for example.

NPs are especially useful because they are very small, inert, bright, and easily modified for conjugation. The nanoscale size and properties of the NPs minimize physical interference with, and optical distortion of, the biological recognition events.

The diameter of a NP of the invention can range from about 1 nm to about 1000 nm or larger. For many applications, it is preferably between about 10 nm to about 300 nm (e.g., about 10, 15, 20, 25, 30, 35, 50, 75, 100, 150, 200, 250, or 300 nm). More preferably, the mean size of the NP of the invention ranges from 1 nm to 300 nm; even more preferably, the mean size of the NP of the invention ranges from 2 nm to 70 nm. In a dispersion of a plurality of NPs, the size distribution preferably has a standard deviation of no more than about 25% (e.g., 1, 2, 3, 5, 10, 15, 20, and 25%) of the average diameter (or largest straight dimension) of the plurality of NPs.

The NPs of the invention can be solid (i.e., substantially without pores). While this form is preferred for many applications, NPs within the invention can also be porous. According to the subject invention, NPs can be synthesized using the processes disclosed in U.S. Pat. Nos. 6,924,116 and 6,548,264, both of which are incorporated by reference in their entirety.

While there are many different types of nanomaterials for bioanalysis, one embodiment of the present invention uses luminophore doped silica NPs. The nature of silica particles enables the relatively easy modification of the surface for conjugation with various biomolecules for a wide range of applications in bioassay systems. These NPs have unique features such as intense luminescent signal, excellent photostability, and easy bioconjugation for linkage between nanomaterials and biological molecules for biological interactions and recognition. In addition, these NPs can be easily prepared and their surfaces can be modified with desired surface properties in both charge and functionality aspects.

In one embodiment, NPs are prepared in two steps. During an initial 24 hour polymerization process, dye-doped silica NPs are formed. In a subsequent post-coating procedure, various functional groups are tightly bound to the NPs. The functional groups present on the surface are particularly suitable for coupling reactions with biological molecules. Each dye-doped NP contains tens of thousands of dye molecules and therefore exhibits a high signal amplification capability. The luminescence intensity ratio of one dye-doped silica NP is approximately $10^4$ times higher than that of one dye molecule. Furthermore, the NPs show excellent photostability.

Both RuBpy and OsBpy dyes are transition-metal-ligand complexes (MLCs); they have long lifetimes and are highly photostable. The double silica coating during the NP preparation process isolates the dye molecules from the outside environment. Because the dye molecules are thereby protected from elements such as solvent molecules and free radicals caused by light exposure, photodecomposition is effectively reduced or eliminated.

The potential to prepare the NPs with existing fluorophores provides a diversity of NPs for various applications. In one embodiment, the signal enhancement of luminescent NPs is based on tens of thousands of luminescent dye molecules contained in each NP. This forms the foundation for luminescence detection with significant optical signal amplification. When excited by an external energy source, the fluorescent dyes emit photons (fluorescence) that are observable and detectable for both quantitative and qualitative analysis.

Thus, in accordance with the subject invention, the recognition of each binding site on the target, such as an antigen on a bacterium surface, can be signaled by one NP containing tens of thousands of dye molecules. Accordingly, the luminescent signals are tens of thousands times higher than those provided by a single dye molecule, thereby providing a highly amplified signal. This is especially suitable for the detection of a single bacterium or very low concentration samples, as well as for target bacteria that have a limited number of surface antigens.

The silica NPs of the subject invention are highly photostable because the dye molecules are encapsulated in a protective silica matrix. The highly luminescent silica NPs facilitate a high level of sensitivity, which reduces or eliminates the need for further target amplification or enrichment of the bacterial samples. Moreover, samples can also be greatly diluted for a reduction in matrix effect.

In certain embodiments of the subject invention, bioconjugated NPs can be incorporated with biorecognition molecules such as antibodies, oligonucleotides, biotin, or streptavidin that are known to bind to particular biomolecules.

In one embodiment, specific monoclonal antibodies are immobilized onto the NP surface to form NP-antibody conjugates. The antibody-conjugated NPs can readily and specifically identify a variety of bacteria (or other cells) through antibody-antigen interaction and recognition. The conjugates bind to the target bacteria when they recognize an antigen on a cell surface, providing a bright luminescent signal for the detection of individual cells. For a bacterium, there are many surface antigens available for specific recognition using antibody-conjugated NPs. Therefore, thousands of NPs can bind to each bacterium, each NP preferably containing thousands of dye molecules, thereby producing a greatly amplified signal.

The present invention includes multiple-luminophore-doped silica NPs with different surface modifications for multiplexed signaling and bioanalysis. These functional NPs can be easily labeled with biomolecules and possess optical encoding capability. By incorporating different amounts of the two luminophores in a single NP, the luminescence intensity ratio can be controlled precisely and made useful for multiple target detection. The procedures are simple, and artificial effects are minimal. Furthermore, dye-doped NPs possess superior advantages of high luminescence intensity for high sensitivity and excellent photostability, which make these NPs especially suitable as biolabeling reagents.

The methods of the present invention are suitable for rapid and sensitive analysis of antigens and nucleic acids and have many potential applications in clinical, food, environmental, and forensic laboratories.

Materials and Methods

Reagents. Tris(2,2'-bipyridyl)osmium(II)bis(hexafluorophosphate) (OsBpy) can be synthesized according to methods known in the art. Tris(2,2'-bipyridyl) dichlororuthenium(II) hexahydrate (RuBpy), 5-Fluorescein isothiocyanate (5-FITC), tetraethyl orthosilicate (TEOS), (3-Aminopropyl) triethoxysilane (APTS), and Triton X-100 (TX-100) are available from Aldrich Chemical Co. Inc. (Milwaukee, Wis.). 5-carboxyrhodamine 6G, succinimidyl ester (5-CR6G, SE), 6-carboxy-X-rhodamine, succinimidyl ester (6-ROX, SE) are from Invitrogen, Co. (Carlsbad, Calif.). THPMP [(3-Trihydroxysilyl)propyl methyl-phosphonate] and CTES [carboxyethylsilanetriol, sodium salt] are available from Gelest, Inc. (Tullytown, Pa.). Cyclohexane, n-hexanol and ammonium hydroxide (28-30 wt %) are available from Fisher Scientific Co. (Pittsburgh, Pa.). Bovine serum albumin (BSA), Tween 20 and MES [2-(N-morpholino)ethanesulfonic acid] are available from Sigma Chemical Co. (St. Louis, Mo.). Purified human IgG and mouse IgG, goat antiserum to human serum, and goat antiserum to mouse serum (forensic) are available from ICN Pharmaceuticals, Inc. (Aurora, Ohio). EZ-Link sulfo-NHS-LC-biotin [Sulfo-succinimidyl-6-(biotinamido) hexanoate], Sulfo-NHS (N-hydroxysulfosuccinimide sodium salt) and EDC [1-ethyl-3-(3-dimethylaminopropyl) carbodiimide hydrochloride] are available from Pierce Chemicals (Rockford, Ill.). Streptavidin-coated microspheres (5.50 µm diameter) and carboxylated silica microspheres (5.06 µm diameter) are available from Bangs Laboratories (St. Louis, Mo.). All other chemicals are of analytical reagent grade. Distilled deionized water (Easy Pure LF) is used for the preparation of all aqueous solutions.

Apparatus. In exemplary embodiments, a Hitachi S-4000 scanning electron microscope (SEM) is used for NP characterization. A Fluorolog TAU-3 spectrofluorometer (Jobin Yvon-Spex, Instruments S.A., Inc. Edison, N.J.) is used to record excitation and emission spectra. Optical and luminescence images are obtained by a laser scanning confocal microscope (Olympus, Japan). FACScan (Becton Dickinson Immunocytometry Systems of San Jose, Calif.) is used for flow cytometric analysis.

It should be understood that the examples and embodiments described herein are for illustrative purposes only and that various modifications or changes in light thereof will be suggested to persons skilled in the art and are to be included within the spirit and purview of this application.

Example 1

Production of Dual Dye Doped Nanoparticle

In one embodiment, RuBpy and OsBpy dyes are prepared in separate aqueous solutions that are then mixed at precisely controlled molar ratios. The final volume of the two-luminophore solution mixture is about 480 µl.

A water-in-oil microemulsion is prepared by mixing about 1.77 ml of TX-100, about 7.5 ml of cyclohexane, about 1.8 ml of n-hexanol, and about 480 µl of the dual-dye mixture solution. TEOS (about 100 µl) is then added as a precursor for silica formation, followed by addition of about 60 µl $NH_4OH$ to initiate the polymerization process. The reaction continues for about 24 hours at room temperature, followed by the addition of about 50 µl of TEOS and either about 10 µl of APTS, about 40 µl of THPMP (for amine modification) or about 50 µl of CTES (for carboxyl modification). The reaction proceeds for about another 24 hours with stirring.

After the reaction is complete, NPs are isolated from the microemulsion using acetone, followed by centrifuging and washing with ethanol and water several times to remove surfactant molecules. Ultrasonication is used during the washing process to remove any physically adsorbed luminophores from the particle surfaces.

While a dual dye doped NP is described in an exemplary embodiment, it is to be understood that more than two dyes may be used.

Example 2

Conjugation of Streptavidin Microspheres with Biotinylated Nanoparticles

In one embodiment, biotin-labeled NPs are prepared by reactions between amine-modified NPs and sulfo-NHS-LC-biotin. Streptavidin-coated microspheres are washed by centrifuging three times with phosphate buffer (pH 8.0) containing about 0.1% Tween-20 and dissolved in the same buffer to a final concentration of approximately $1.0 \times 10^8$ particles/ml.

A series of microsphere solutions containing different numbers of particles are prepared and added to an aliquot of excess biotin-NP solution. Each suspension is gently shaken at room temperature for about 2 hours and analyzed with a Becton Dickinson FACScan flow cytometer using Argon laser excitation at 488 nm. Orange (585 μm) and red (>650 nm) luminescence channels are monitored. All solutions pass through the flow cytometer at the same flow rate (60 μl/min) and for the same time period (3 minutes).

Example 3

Covalent Coupling of Antibodies to Carboxylated Microspheres and Nanoparticles In one embodiment, free carboxylic acid groups on NPs are crosslinked with amine-containing antibodies.

Briefly, about 100 μl of a 0.22% (w/v) suspension of COOH-modified NPs are washed by centrifuging once with deionized water. The pellet is then resuspended in about 1 ml of 0.1 M MES, pH 5.5. Aqueous solutions of 10 mM Sulfo-NHS and 4 mM EDC dissolved in MES buffer are freshly prepared, and about 0.5 ml of each solution is added to the NP solution immediately. The NPs are incubated at room temperature with gentle agitation. After about 15 minutes, the NPs are centrifuged and washed with 10 mM phosphate buffer, pH 7.4.

After resuspension in about 1.5 ml phosphate buffer, the NPs are added to about 50 μl of antibodies at a concentration of 1 mg/ml. The mixture is incubated at room temperature for about 2 hours with gentle end-to-end shaking.

The NPs are washed in 10 mM phosphate buffer and then resuspended in quenching solution (40 mM Tris-HCl with 0.05% (w/v) BSA) for about 60 minutes to block free carboxylates. Protein coated NPs are purified by alternately centrifuging and resuspending in phosphate buffer (10 mM, pH 7.4) with 1% BSA and stored at about 4° C. until used.

Covalent coupling of secondary antibodies to carboxylated silica microspheres follows the same procedures.

Example 4

Conjugation of Antibody-Nanoparticles with Secondary Antibody-Microspheres

In one embodiment, antibody-conjugated NPs and secondary-antibody-modified microspheres are diluted in an incubation buffer (10 mM phosphate buffer, pH 7.4, 1% BSA, 0.05% Tween-20), mixed at an experimentally optimized ratio (500:1) and gently shaken at room temperature for about 30 minutes.

The resultant product is washed three times by centrifugation (500 rpm, 10 minutes), resuspended in the same buffer and stored at 4° C. Luminescence from the NP-coated microspheres is measured with a commercial laser scanning confocal microscope.

An Argon ion laser excited at 488 nm wavelength and two orthogonal detection channels, for RuBpy and OsBpy, respectively, are detected with two distinct photomultiplier tubes. Both orange and red channels are saved as 24-bit TIF images.

Example 5

Flow Cytometry Multiplex Detection

In one embodiment, NPs with luminescence intensity ratios of 9:1 and 2:1 (610 nm; 710 nm) are conjugated with human IgG and mouse IgG, respectively. The same number of anti-mouse IgG and anti-human IgG coated microspheres ($1.62 \times 10^{-17}$ mol) are mixed with optimized amounts of mouse IgG and human IgG labeled nanoparticles ($8.1 \times 10^{-15}$ mol). The mixture is diluted with diluent buffer and passed through the flow cytometer.

Example 6

Dual Dye Nanoparticle Characterization

FIG. 1 shows the excitation and emission spectra of RuBpy and OsBpy dyes on a spectrofluorometer. Line "a" charts an excitation spectrum of RuBpy at 610 nm emission; line "b" charts an excitation spectrum of OsBpy at 710 nm emission; line "c" illustrates an emission spectrum of RuBpy at 488 nm excitation; and line "d" illustrates an emission spectrum of OsBpy at 488 nm excitation. These two dyes share a broad overlapping excitation spectrum, but have two distinct maximum emission wavelengths, with RuBpy at 610 nm and OsBpy at 710 nm. By doping these two dyes at certain molar ratios, the NPs provide controllable peak intensity ratios at 610 nm and 710 nm, upon single wavelength excitation.

Figure 2:
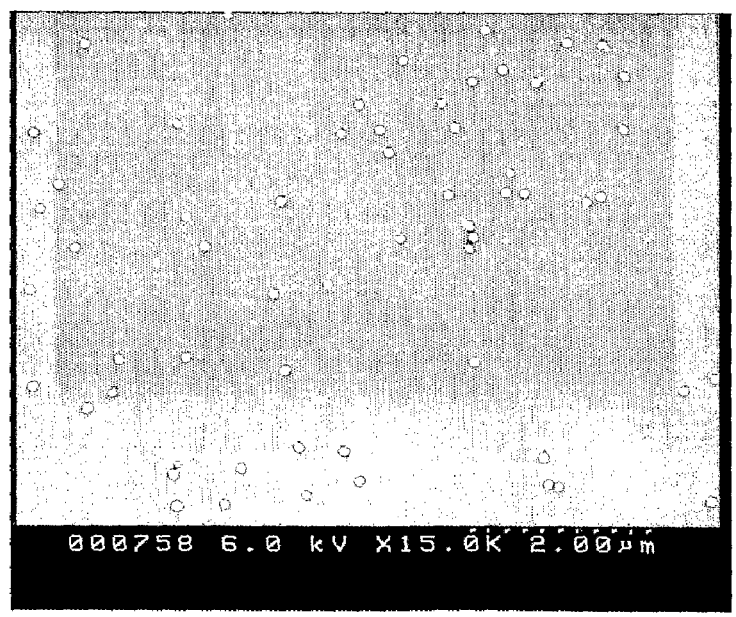
FIG. 2 is a scanning electron microscopy (SEM) image of dual luminophore-doped carboxyl-functionalized NPs.

FIG. 2 is a scanning electron microscopy (SEM) image of dual luminophore-doped carboxyl-functionalized NPs. The diameter of each of the carboxyl group modified NPs is about 70±3 nm, as characterized by SEM. The amine modified NPs are of similar size. The functionalized NPs are dispersed very well in aqueous solutions, and no aggregation was observed due to the electrostatic repulsion force between the NPs. The carboxyl group modified NPs are negatively charged at neutral pH, and the inert phosphonate groups on the amine modified NPs also result in an overall negative surface charge that prevents NP coagulation.

Figure 3A:
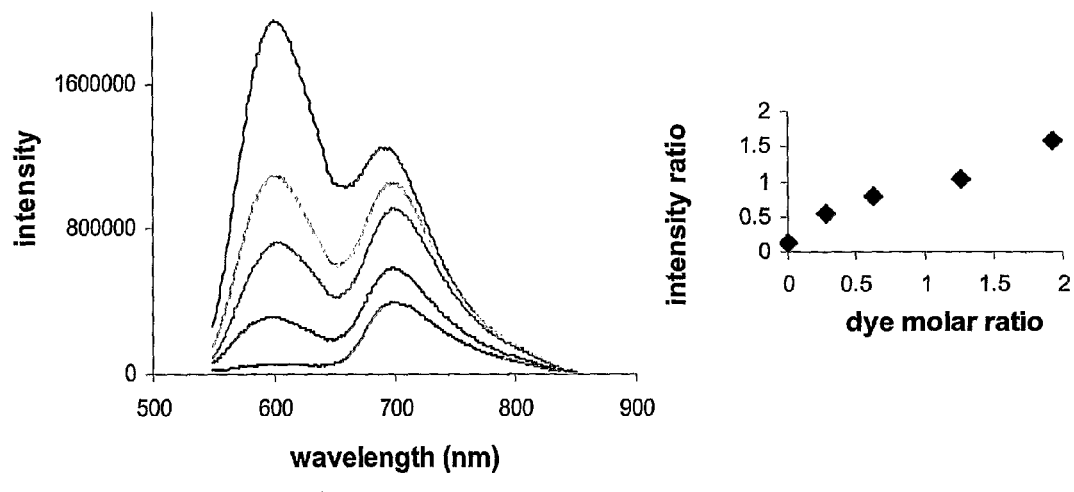
FIG. 3a illustrates the emission spectra of several representative dual-luminophore-doped NP samples.

The luminescence intensity ratio of dual dye NPs can be precisely controlled by varying the doping amount of the two dyes. FIG. 3a illustrates the emission spectra of several NP samples with varying doping amounts of two dyes. The inset for FIG. 3a shows good correlation between the intensity ratio and the molar ratio of the two dyes. To determine whether the intensity ratios have batch-to-batch reproducibility, the average peak intensity ratios from five parallel NP solutions are compared; the coefficient of variation is 7%, indicating that as long as the intensity ratios differ from each other by 14%, the NPs can be fully distinguished during multiplexed detection.

Figure 3B:
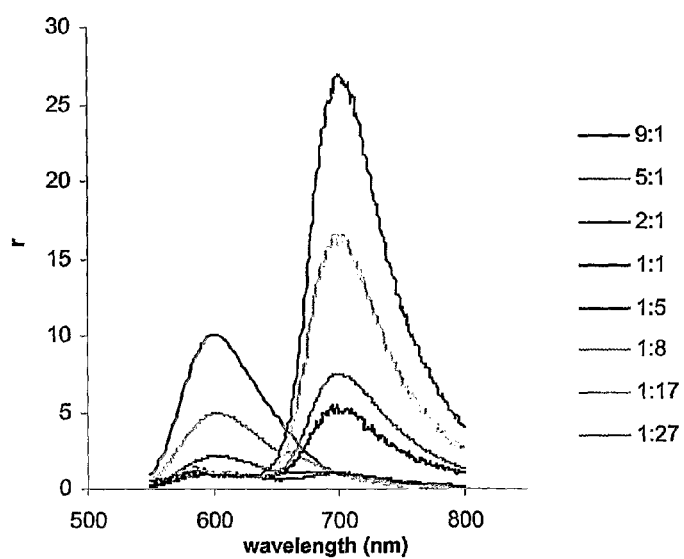
FIG. 3b shows the normalized emission spectra of eight representative dual-luminophore-doped NP samples.

With this information, a new batch of NP samples without peak ratio overlapping can be prepared. FIG. 3b shows the normalized emission spectra of NP samples with different doping concentrations for the two dyes. The Y-axis shows peak luminescence intensity ratios of 610 nm and 710 nm. By controlling the doping concentration of these two dyes, varying intensity ratios including, for example, 9:1, 7:1, 5:1, 2:1, 1:1, 1:5, 1:8, 1:17, and 1:27 (488 nm excitation) are obtained; they all differ from each other by more than 14%. More ratio combinations can be obtained by changing the doping amount of the two dyes (RuBpy/OsBpy), making true multiplex signaling possible and feasible.

Example 7

Ligand Binding System Using Biotin-Nanoparticles and Streptavidin-Microspheres In one embodiment, the dual dye NPs are used in multiple signaling applications with biotin and avidin. Biotin is a relatively small molecule which has high affinity to avidin and streptavidin ($K_a = 1.3 \times 10^{15}$ M$^{-1}$). The coupling reaction is rapid and once the bond is formed, it is unaffected by most changes such as pH, organic solvents and other denaturing agents. In this embodiment, biotin-labeled NPs and streptavidin-conjugated microspheres are mixed at an appropriate molar ratio. Avidin-biotin interaction enables NP assembly on the microsphere surfaces. This assembly is employed initially as a simplified ligand binding system before conducting multiplexed detection.

Amine-modified NPs are reacted with the activated ester of biotin to couple biotin molecules to the NPs. To determine the efficiency of the conjugation, TMR-labeled avidin is mixed with varying quantities of either biotinylated or unbiotinylated NPs. The luminescence intensity of the supernatant solution as a function of the added quantity of NP is explored and demonstrates the successful biotinylation. Streptavidin-coated microspheres are allowed to react with these biotinylated NPs.

The number of NPs that pack onto the microsphere surfaces is estimated by dividing the theoretical microsphere surface area by the cross-sectional area of a plane bisecting one NP. The resulting value is used to determine the minimum number of NPs needed in suspension for each microsphere. The calculated value is 25,000:1 in this case. In one embodiment, a 50,000:1 ratio is used to ensure sufficient saturation of the microsphere surface.

Figures 4A, 4B:
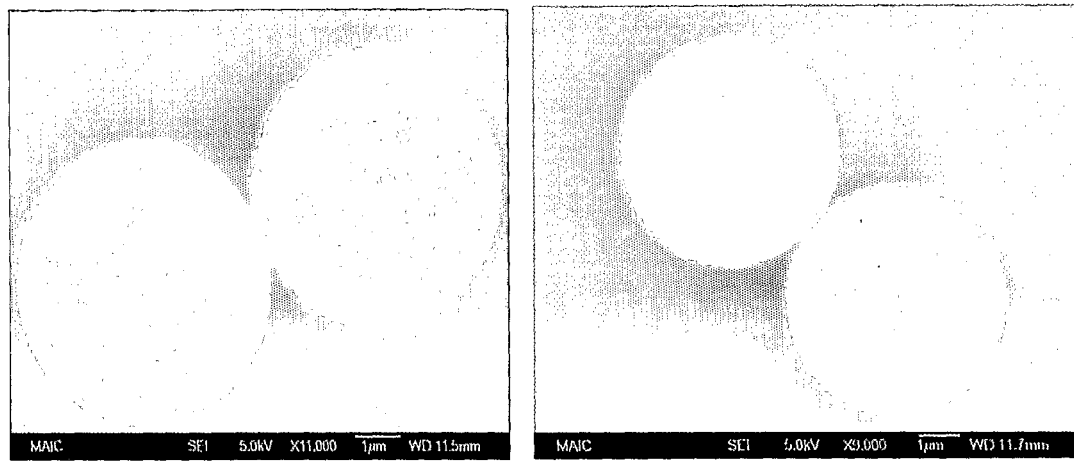
FIG. 4a is an SEM image of 70 nm biotin-labeled NPs assembled onto 5.5 μm diameter streptavidin-coated silica microspheres.
FIG. 4b is an SEM image of 70 nm non-biotinylated NPs assembled onto 5.5 μm diameter streptavidin-coated silica microspheres.

An SEM image of 70 nm biotin-labeled NPs assembled onto a 5.5 μm diameter streptavidin-coated silica microspheres is shown in FIG. 4a. The biotinylated NPs attached to the microspheres, clearly demonstrating binding between biotin and streptavidin. In contrast, there were only minimal NPs on the microsphere surface when the microspheres were treated with non-biotinylated NPs (FIG. 4b).

Figure 5:
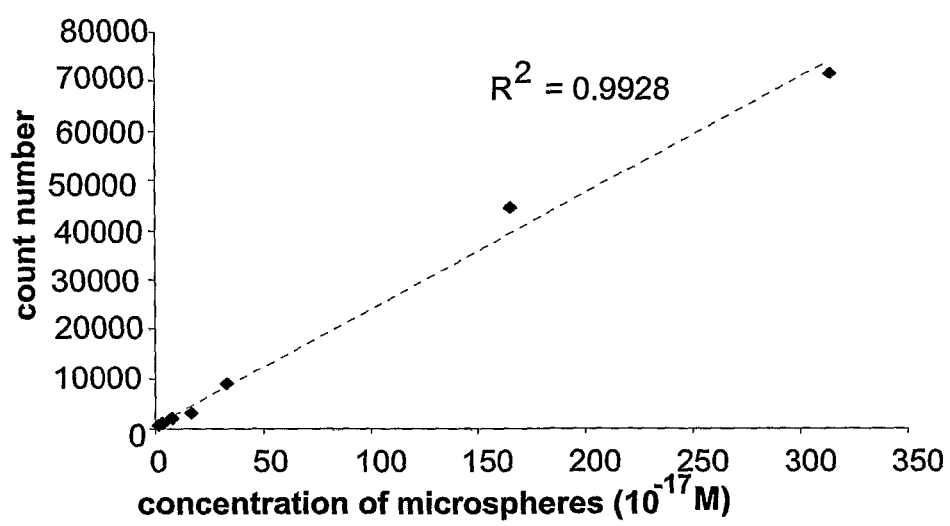
FIG. 5 shows the counted events obtained from dot plots as a function of the theoretical concentration of the prepared microsphere solutions.

Flow cytometry experiments are performed using these NP-coated microspheres. Different concentrations of microsphere solutions are mixed with an aliquot of excess biotin-labeled NPs to ensure the successful coating of each microsphere. Bead suspensions are dispersed by vortexing before analysis. A flow cytometer analyzes individual microspheres by size and luminescence. Orange and red luminescence are used for microsphere classification, with the ratio correlating to the peak intensity ratio at 610 nm and 710 nm measured with a spectrofluorometer. FIG. 5 shows the counted events obtained from dot plots of streptavidin microspheres coated with biotinylated NPs as a function of the theoretical concentration of the prepared microsphere solutions. Because each solution in this example passes through the flow cytometer at the same flow rate and for the same time period, the counted number should have a linear relationship with the theoretical concentrations. FIG. 5 demonstrates this linear relationship. This model system shows that the NPs are employed successfully for target labeling and counting, and the application can be extended to multiplexed immunoassays.

Example 8

Dual-Luminophore-Doped Silica Nanoparticles for Multiplexed Immunoassays

One embodiment of the invention includes a system for multiplexed immunoassays using dual-dye NPs. Antibody conjugated NPs with varying intensity ratios and secondary antibody coated microspheres are used for specific immunoassay recognition. The NP/microsphere interaction simulates the recognition process between conjugated NPs and potential receptors/antigens on the surface of a cell or bacterium.

Two individual analytes are used for multiplexed immunoassays. Mouse IgG and human IgG are respectively conjugated to NPs using a carbodiimide-based reaction; goat anti-mouse IgG and goat anti-human IgG are immobilized onto microspheres in a similar way. To verify that the mouse IgG has been successfully conjugated with the NPs, control experiments are performed by adding BSA to replace mouse IgG during the bioconjugation step, followed by addition of TMR-labeled goat anti-mouse IgG. The assembly is centrifuged, and the pellets are dissolved in the phosphate buffer. TMR-labeled goat anti-mouse IgG will specifically bind to mouse IgG conjugated NPs and non-specifically bind to BSA conjugated NPs. The pellets are excited at 545 nm to observe the emission of TMR molecules labeled on the NPs. The substantially higher luminescence intensity from mouse-IgG-coated NPs incubated with TMR-labeled goat anti-mouse IgG verifies the successful binding of antibody on the NP surface.

In one embodiment, before performing a multiplexed detection, the parameters of each assay are optimized separately in a non-multiplexed format. Individual sets of NPs are conjugated with the target microspheres required for each reaction. After centrifuging and washing, the product is resuspended in buffer solution and mounted on a microscope slide for imaging.

Because the methods used to control the assembly process involve specific biochemical interactions, verification that the assembled composites are the result of these specific interactions between the particles, and not of nonspecific interactions, is performed in one embodiment. Two sets of antibody-coated NPs and two sets of secondary antibody-coated microspheres are cross reacted following the same procedure mentioned above. To reduce nonspecific binding, the incubation buffer contains 1% BSA and 0.05% Tween-20, incubation time is limited to 30 minutes, and the molar ratio of NPs to microspheres is optimized to achieve an optimal S/N ratio. The optimized molar ratio of NPs to microspheres is determined to be 500:1. Confocal luminescence images of microspheres coated with NPs under specific or non-specific reaction conditions are observed.

Figure 6A:
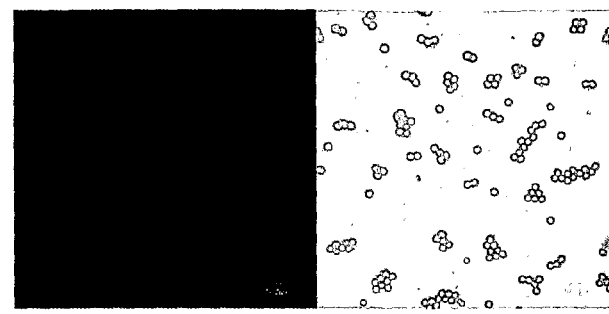
FIG. 6a shows specific binding between anti-mouse IgG conjugated microspheres with mouse IgG conjugated NPs.
Figure 6B:
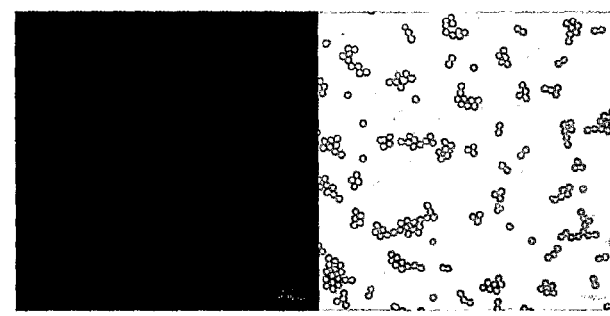
FIG. 6b shows nonspecific binding between anti-human IgG conjugated microspheres with mouse IgG conjugated NPs.
Figure 6C:
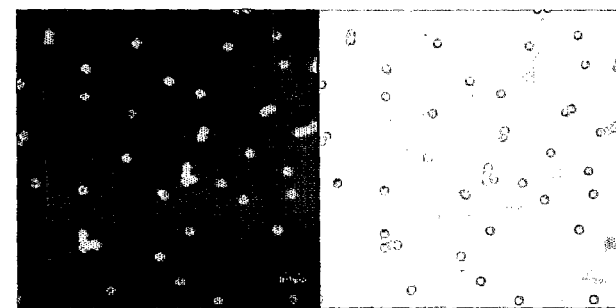
FIG. 6c shows specific binding between anti-human IgG conjugated microspheres with human IgG conjugated NPs.
Figure 6D:
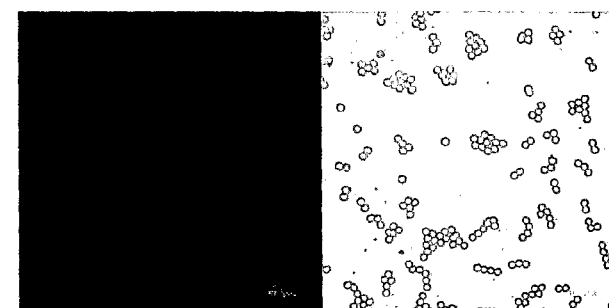
FIG. 6d shows nonspecific binding between anti-mouse IgG conjugated microspheres with human IgG conjugated NPs.

FIG. 6a shows specific binding between anti-mouse IgG conjugated microspheres with mouse IgG conjugated NPs; FIG. 6b shows nonspecific binding between anti-human IgG conjugated microspheres with mouse IgG conjugated NPs; FIG. 6c shows specific binding between anti-human IgG conjugated microspheres with human IgG conjugated NPs; and FIG. 6d shows nonspecific binding between anti-mouse IgG conjugated microspheres with human IgG conjugated NPs. Thus, specific binding between anti-mouse IgG-microspheres with mouse IgG-NPs (FIG. 6a) and specific binding between anti-human IgG-microspheres with human IgG-NPs (FIG. 6c) are observed, while nonspecific binding between anti-human IgG-microspheres with mouse IgG-NPs (FIG. 6b) and nonspecific binding between anti-mouse IgG-microspheres with human IgG-NPs (FIG. 6d) are insignificant.

Figure 7:
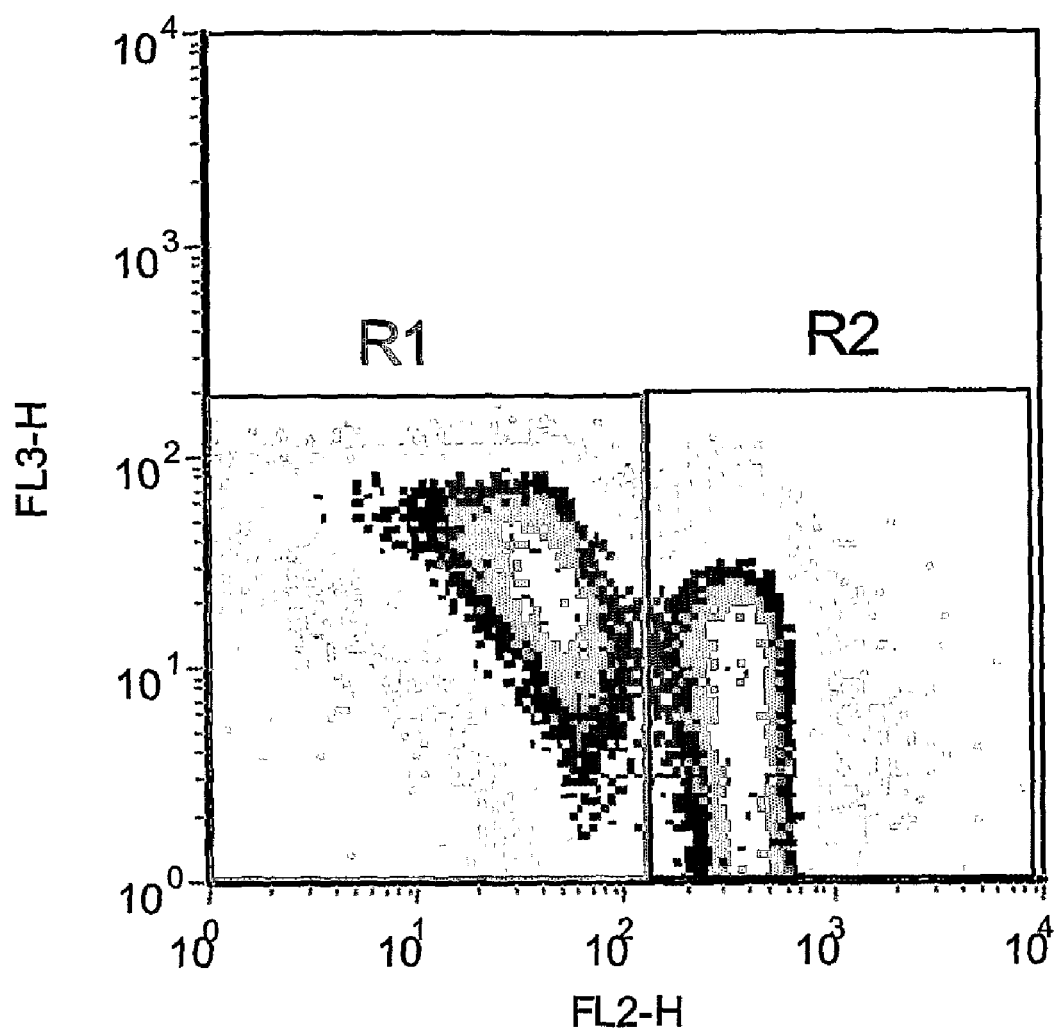
FIG. 7 is a two-dimensional dot plot showing classification of the two microsphere sets based on simultaneous analysis of logarithmic orange luminescence (FL2) and logarithmic red luminescence (FL3) on a flow cytometer.

Using these two sets of microspheres, a proof-of-concept flow cytometry experiment is conducted for the detection of mixtures of analytes with dual luminophore-doped silica NPs. Two kinds of fluorescent NPs are chosen with intensity ratios (610 nm:710 nm) of 9:1 and 2:1 and then labeled with human IgG and mouse IgG, respectively. The same number of anti-mouse-IgG- and anti-human-IgG-coated microspheres ($1.62 \times 10^{-17}$ mol, respectively) are mixed with these two kinds of IgG coated NPs ($8.1 \times 10^{-15}$ mol, respectively) to form a cocktail. FIG. 7 is a two-dimensional dot plot showing classification of the two microsphere sets based on simultaneous analysis of logarithmic orange luminescence (FL2) and logarithmic red luminescence (FL3) on a flow cytometer. The dots in the R1 region represent anti-mouse IgG microspheres coated with mouse IgG NPs (2:1 ratio), and those in the R2 region represent anti-human IgG microspheres coated with human IgG NPs (9:1 ratio). The numbers of the dots in the two regions are counted. One would expect to find equal numbers of microspheres in the two regions because the same number of microspheres were used in each region. Experimental results show that the population distribution is 46.56% and 53.42%, respectively, in R1 and R2 regions, which correlates well with the expected value when possible binding affinity differences are considered. Thus, the system of the present invention is useful for the multiplexed detection of microspheres by bioconjugated NPs. These NPs can be applied for bacteria/cell recognition, especially those with minimal specific antigens where dye molecules encounter problems. These NPs can bridge this gap due to the following reasons: (1) the higher luminescence intensity of NPs improves the detection limit, especially for some targets which have limited number of surface antigens and (2) the NPs are highly photostable due to the silica matrix protection, while dye molecules suffer from severe photobleaching problems.

The emission peak ratios of the NPs used are 9:1 and 2:1. However, FIG. 7 suggests a small overlap in the measurement space that may potentially result in misclassifications of some microspheres from adjacent sets and limit the multiplex capability. The overlap is due to the collection efficiency of the optical filter configuration selected for the flow cytometer measurements. The filters used in the FACScan are a band pass filter (585±42 nm) for an orange luminescence channel and a long pass filter (>650 nm) for a red luminescence channel, neither of which was optimized for RuBpy or OsBpy dye (in the case where the flow cytometer is a multiuser facility and changes of the optical system are not permitted). Multiplex detection capability can be improved with a more appropriate set of filters.

Example 9

Production of Triple-Luminophore-Doped Silica Nanoparticles (FRET Nanoparticles)

In one embodiment, triple-luminophore-doped silica NPs are prepared through a two-step Stöber process. In the first step, three types of amine reactive dyes [5-Fluorescein isothiocyanate] (5-FITC), [5-carboxyrhodamine 6G, succinimidyl ester] (5-CR6G, SE), [6-carboxy-X-rhodamine, succinimidyl ester] (6-ROX, SE) are dissolved in anhydrous DMF, respectively, added an excess of APTS, and stirred for 24 h in the dark. In the second step, the three dye solutions are mixed at desired ratios and added to a clean glass reaction vessel containing ethanol and ammonium hydroxide. The mixture was slowly stirred for 24 h. TEOS is added afterwards and stirred for another 24 h. After the reaction, the samples are centrifuged at 14,000 rpm for 30 min to collect the silica NPs. The NPs are further washed with ethanol and phosphate buffer by centrifugation and decantation several times in order to remove unreacted chemicals.

It should be understood that other types of dyes can also fit for this system and more than three dyes can be used.

Example 10

Multiple Color FRET Nanoparticles for Multiplexed Optical Signaling

Figure 8:
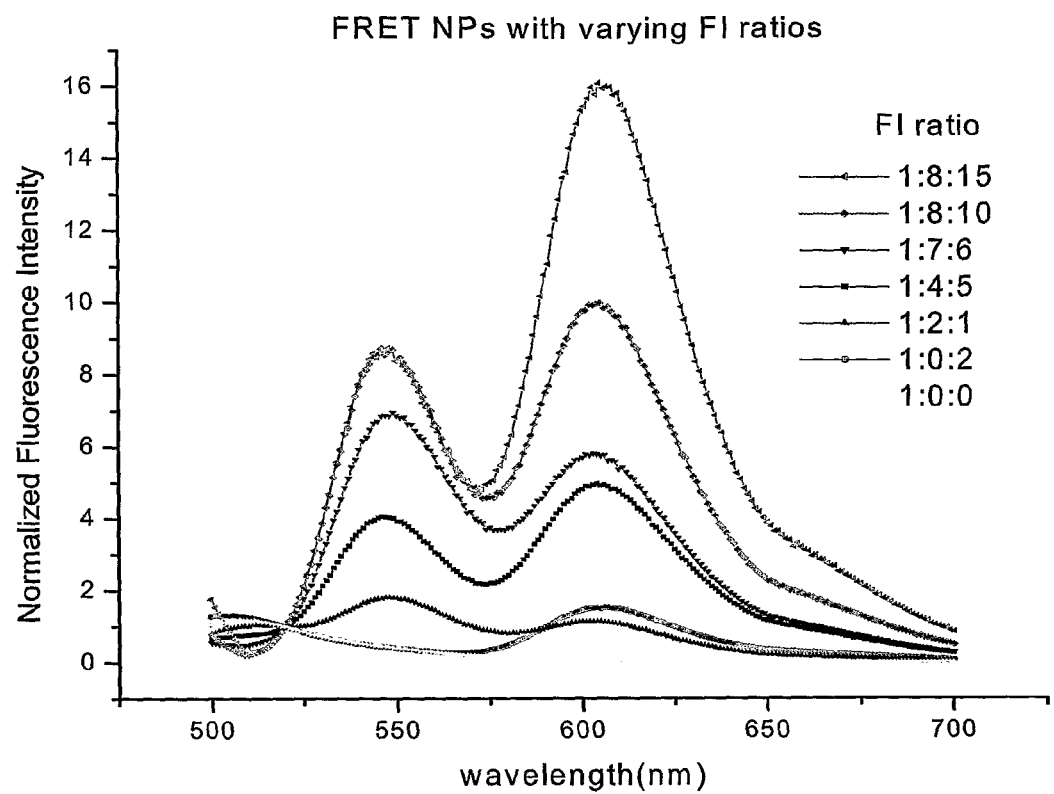
FIG. 8 shows the normalized emission spectra of FRET NP samples.
Figure 9:
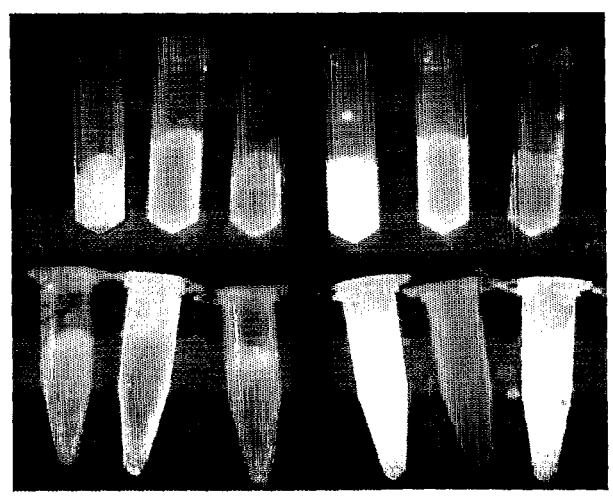
FIG. 9 displays the color of FRET NP samples under UV illumination.
Figure 10:
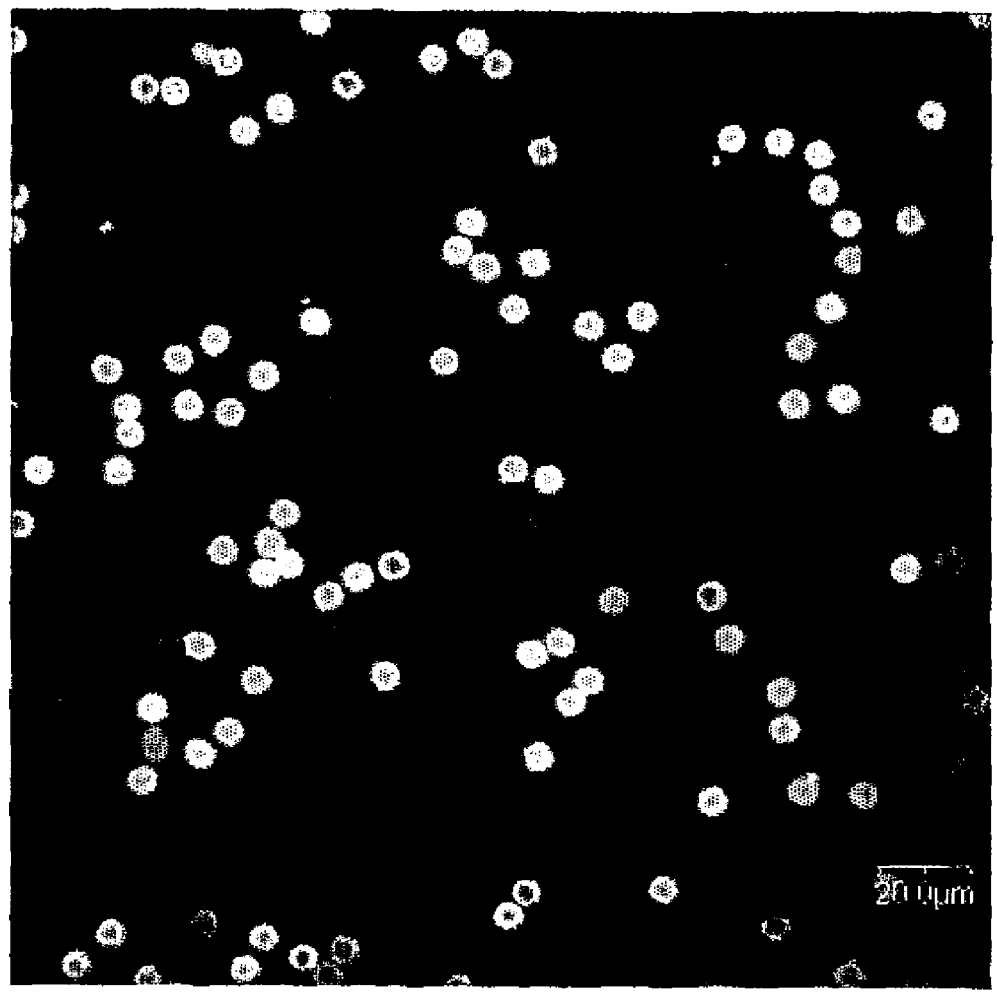
FIG. 10 shows the confocal fluorescence image of five kinds of microsphere-NP complexes with single wavelength excitation.

One embodiment of the invention includes a system for multiplexed optical signaling using triple-luminophore-doped silica NPs. Three types of organic luminophores are doped inside the same NPs at varying ratios. By virtue of fluorescence energy transfer of the luminophores, single wavelength excitation can generate tunable emission signatures of the NPs. FIG. 8 represents the normalized emission spectra of FRET NP samples with varying concentrations of the three dyes. More ratio combinations can be obtained by changing the doping amount of the three dyes. Different NPs can display varying colors under UV illumination, as shown in FIG. 9. Five kinds of different colored NPs are labeled with biotin molecules, and conjugated with streptavidin conjugated microspheres, FIG. 10 shows the confocal fluorescence image of microsphere-NP complexes which generate five distinguishable colors under single wavelength excitation. This demonstrates that simultaneous identification of multiple bacterial pathogens can not only be performed by flow cytometry assays using dual-luminophore doped NPs, but also be detected conveniently under optical microscopy with multiple-color FRET. Each type of NP is modified with one specific antibody and mixed with bacteria samples. Single wavelength excitation with distinguished multiple colors of the NPs enable high-throughput detection of multiple bacteria at the same time.

The advantage of color tunability under single wavelength excitation also makes the FRET NPs useful in making NP monolayers for display, and in fabricating composite electro-optic devices. The NP morphology change leads to enhanced current density and radiance. The colors of light produced by NPs are much more saturated than that of other sources.

Multicolor optical coding using luminescent NPs offers several advantages such as high signal amplification, excellent optical stability and easy bioconjugation. The multiplexed analysis can be carried out directly at the nanometer dimension level using the newly developed NPs, thereby minimizing artificial interferences. The dye-doped NPs are highly sensitive, which allows for particle detection even at a very low target concentration. The luminescence intensity of one NP is about $10^4$ times higher than that of a single dye molecule. This advantage makes NP labeling especially suitable in low target concentration situations. Combined with flow cytometry assays, this method proves to be rapid, selective and sensitive. The present invention offers great flexibility and efficiency in clinical surveillance and detection of infectious diseases, such as rapid diagnosis of multiple bacteria and viruses.

All patents, patent applications, provisional applications, and publications referred to or cited herein are incorporated by reference in their entirety, including all figures and tables, to the extent they are not inconsistent with the explicit teachings of this specification.

We claim:

1. A nanoparticle comprising at least two inorganic luminophores each with different emission wavelengths, wherein a specific molar ratio of the luminophores is encapsulated in a silica matrix, wherein the specific molar ratio of luminophores controls intensity of the emission wavelengths generated from the silica matrix when exposed to a single wavelength excitation, wherein the luminophores are Tris(2,2'-bipyridyl)osmium(II) bis(hexafluorophosphate) (OsBpy) and Tris(2,2'-bipyridyl)dichlororuthenium(II) hexahydrate (RuBpy) and wherein the molar ratio of luminophores is selected from the group consisting of: 9:1, 7:1, 5:1, 2:1, 1:5, 1:8, 1:17, and 1:27.

2. The nanoparticle of claim 1, wherein the diameter of the nanoparticle is between about 1 nm and about 300 nm.

3. The nanoparticle of claim 1, wherein the diameter of the nanoparticle is between about 2 nm and about 70 nm.

4. The nanoparticle of claim 1, wherein the silica matrix comprises a functional group.

5. The nanoparticle of claim 4, wherein the functional group is a biorecognition molecule selected from the group consisting of: antibodies, oligonucleotides, biotin, and streptavidin.

6. The nanoparticle of claim 5, wherein the functional group is biotin.

7. The nanoparticle of claim 5, wherein the functional group is an IgG antibody.

8. The nanoparticle of claim 5, wherein the functional group is streptavidin.

9. A composition comprising a plurality of nanoparticles according to claim 1.

* * * * *

UNITED STATES PATENT AND TRADEMARK OFFICE
CERTIFICATE OF CORRECTION

| | |
|---|---|
| PATENT NO. | : 8,168,447 B2 |
| APPLICATION NO. | : 12/066308 |
| DATED | : May 1, 2012 |
| INVENTOR(S) | : Weihong Tan et al. |

It is certified that error appears in the above-identified patent and that said Letters Patent is hereby corrected as shown below:

Column 7,
Line 1, "(585 μm)" should read --(585 nm)--

Signed and Sealed this
Seventh Day of August, 2012

David J. Kappos
*Director of the United States Patent and Trademark Office*